US006395495B1

(12) United States Patent
Montagnier et al.

(10) Patent No.: US 6,395,495 B1
(45) Date of Patent: May 28, 2002

(54) METHODS AND KITS FOR DETECTING ANTIBODIES AGAINST AN HIV VARIANT

(75) Inventors: Luc Montagnier, Le Plessis-Robinson; Jean-Claude Chermann, Elancourt; Francoise Barre-Sinoussi, Issy les Moulineaux; Christine Rouzioux, Paris; Willy Rozenbaum, Paris; Charles Dauguet, Paris; Jacqueline Gruest, L'Hay les Roses; Marie-Therese Nugeyre; Francoise Rey, both of Paris, all of (FR); Robert C Gallo; Mikulas Popovic, both of Bethesda, MD (US); Mangalasseril G Sarngadhar, Vienna, VA (US); Claudine Axler-Blin; Solange Chamaret, both of Paris (FR)

(73) Assignees: Institut Pasteur, Paris (FR); The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/437,126

(22) Filed: Nov. 10, 1999

Related U.S. Application Data

(63) Continuation of application No. 08/424,631, filed on Apr. 19, 1995, which is a division of application No. 08/019,297, filed on Feb. 18, 1993, which is a division of application No. 07/876,297, filed on Apr. 30, 1992, now abandoned, which is a continuation of application No. 07/117,937, filed on Nov. 5, 1987, now Pat. No. 5,135,864, which is a continuation of application No. 06/785,638, filed on Oct. 8, 1985, now Pat. No. 4,708,818, which is a continuation of application No. 06/558,109, filed on Dec. 5, 1993, now abandoned.

(30) Foreign Application Priority Data

Sep. 15, 1983 (GB) ................................................ 24800

(51) Int. Cl.$^7$ ............................................... G01N 33/53
(52) U.S. Cl. .................................. 435/7.1; 435/5
(58) Field of Search .................. 435/5, 7.1; 424/188.1, 424/208.1

(56) References Cited

U.S. PATENT DOCUMENTS

| | | | |
|---|---|---|---|
| 4,323,555 A | 4/1982 | Theilen |
| 4,520,113 A | 5/1985 | Gallo et al. |
| 4,708,818 A | 11/1987 | Montagnier et al. |
| 4,843,011 A | 6/1989 | Sarngadharan et al. |
| 5,156,949 A | 10/1992 | Luciw et al. |

FOREIGN PATENT DOCUMENTS

| | | |
|---|---|---|
| EP | 0116949 | 8/1984 |
| SU | 0745948 | 7/1980 |

OTHER PUBLICATIONS

English Language Abstract of Soviet Union Patent No. 0,745,948.
Barre–Sinoussi et al., Science, 200, pp. 868–871 (1983).
Gallo et al., J. Nat'l. Cancer Inst., 69(6), pp. 1209–1214 (1982).
Barre–Sinoussi et al., Ann. Microbiological. (Institut Pasteur), 130 B, pp. 349–362 (1979).
Poiesz et al., Proc. Nat'l. Acad. Sci., USA, 77(12), pp. 7415–7419 (1980).
Robert–Guroff et al., J. Exp. Med., 154, pp. 1957–1964 (1981).
Kalyanaraman et al., J. Virol., 38, pp. 906–915 (1981).
Popovic et al., Science, 219, pp. 856–859 (1983).
Montelaro et al., J. of Virology, 42(3), pp. 1029–1038 (1982).
Montagnier et al., "A New Human T–Lymphotropic Retrovirus . . .", reprinted from Human T–Cell Leukemia/Lymphoma Viruses, Cold Spring Harbor Laboratory, Gall et al., eds., pp. 363–379 (1984).
Kalyanaraman et al., Science, 225, pp. 321–323 (1984).
Casey et al., J. of Virology, 55(2), pp. 417–423 (1985).
Saxinger et al., Laboratory Investigation, 49(3), pp. 371–377 (1983).
De The' et al., C.R. Acad. Sc. Paris, t. 297, Serie III, pp. 195–197 (1983).
Renato Dulbecco, Oncogenic Viruses, Microbiology, Third Edition, pp. 1231–1261 (Harper & Row Publishers, 1980).
Chandra et al., Cold Spring Harbor Conference, Cell Proliferation, vol. 7, pp. 775–791 (1980).
Schetters et al., Infection and Immunity, 29(3), pp. 972–980 (1980).
Rho et al., Virology, 112, pp. 355–360 (1981).
Posner et al., J. of Exp. Med., 154, pp. 333–346 (1981).
Poiesz et al., Nature, 294, pp. 268–271 (1981).
Kalyanaraman et al., Nature, 294, pp. 271–273 (1981).
Miyoshi et al., Nature, 294, pp. 770–771 (12981).
Essex, Epidemiological Reviews, 4, pp. 189–203 (1982).
Oroszlan et al., Proc. Nat'l. Acad. Sci., USA, 79, pp. 1291–1294 (1982).
Morbidity and Mortality Weekly Report, 31(19), pp. 249–251 (1982).

(List continued on next page.)

*Primary Examiner*—Laurie Scheiner
*Assistant Examiner*—Jeffrey S. Parkin
(74) *Attorney, Agent, or Firm*—Finnegan, Henderson, Farabow, Garrett & Dunner, L.L.P.

(57) ABSTRACT

The invention concerns a retrovirus extract containing a p25 protein which recognizes immunologically sera of patients afflicted with lymphadenopathy syndrom (LAS) or acquired immune deficiency syndrom (AIDS). It relates to a method and kit for in vivo assay of LAS or AIDS involving contacting sera from patients to be diagnosed for such diseases with said retrovirus extract and by detecting the immunological reaction, if any.

14 Claims, 1 Drawing Sheet

OTHER PUBLICATIONS

Yamamoto et al., Science, 217, pp. 737–739 (1982).
Morbidity and Mortality Weekly Report, 31(37), pp. 507–514 (1982).
Blattner et al., Int. Journal of Cancer, 30, pp. 257–264 (1982).
Gallo et al., Blood, 60(3), pp. 545–557 (1982).
Essex, J. of the National Cancer Institute, 69(4), pp. 981–985 (1982).
Robert–Guroff et al., Virology, 122, pp. 297–305 (1982).
Haynes et al., J. of Exp. Med., 157, pp. 907–920 (1983).
Sarin, et al., Proc. Natl. Acad. Sci., USA, 80, pp. 2370–2374 (1983).
Haynes et al., Proc. Natl. Acad. Sci., USA, 80, pp. 2054–2058 (1983).
Reitz et al., Virology, 126, pp. 688–692 (1983).
Morbidity and Mortality Weekly Report, 32(18), pp. 233–234 (1983).
Marx, Science, 220, pp. 806–809 (1983).
Trainin et al., Science, 220, pp. 858–859 (1983).
Essex et al., Science, 220, pp. 859–862 (1983).
Gallo et al., Science, 220, pp. 865–867 (1983).
Journal of the American Medical Association, 249(21), pp. 2878–2879 (1983).
De Jong et al., The Lancet, pp. 1293–1296 (1983).
Morbidity and Mortality Weekly Report, 32(24), pp. 309–311 (1983).
Seiki et al., Proc. Natl. Acad. Sci., USA, 80, pp. 3618–3622 (1983).
Weinberg, Hospital Practice, pp. 13, 17–18 (Jul. 1983).
Evatt et al., The Lancet, 2, pp. 698–700 (1983).
Essex et al., Science, 221, pp. 1061–1064 (1983).
Montagnier et al., Ann. Virol. (Inst. Pasteur), 135E, pp. 119–134 (1984).
Des Jarlais et al., Morbidity and Mortality Weekly Report, 33(27), pp. 377–379 (1984).
Cheingsong–Popov et al., The Lancet, pp. 477–480 (1984).
Feorino et al., Science, 225, pp. 69–72 (1984).
Shaw et al., Science, 226, pp. 1165–1171 (1984).
Alizon et al., Nature, 312, pp. 757–760 (1984).
Marx, Science, 227, pp. 156–157 (1985).
Marx, Science, 227, p. 503 (1985).
Rabson et al., Cell, 40, pp. 477–480 (1985).
Sarngadharan et al., Proc. Natl. Acad. Sci., USA, 82, pp. 3481–3484 (1985), cited in Biosis Abstract No. 80059454.
Neurath et al., J. of Virol. Methods, 11, pp. 75–86 (1985).
Di Marzo Veronese et al., Proc. Natl. Acad. Sci., USA, 82, pp. 5199–5202 (1985).
Wong–Staal et al., Science, 229, pp. 759–762 (1985).
Wong–Staal et al., Nature, 317, 395–403 (1985).
Norman, Science, 230, pp. 518–521 (1985).
Metzler, Biochemistry, pp. 135–137 (Academic Press, London, 1977).
Weber et al., Methods in Enzymology, vol. xxvi, pp. 3–27 (Academic Press, New York, 1972).
Ratner et al., Nature, 313, pp. 636–637 (1985).
Coffin et al., Science, 228, pp. 697 (1986).
Alberts et al., Eds., Molecular Biology of the Cell, pp. 165–173 (Garland Publishing, New York & London, 1983).

Maniatis et al., Eds., Molecular Cloning, A Laboratory Manual, pp. 80–95 (Cold Spring Harbor Laboratory, 1982).
Schmidt, Diagnostic Procedures for: Viral, Rickettsial and Chlamydial Infections, Fifth Edition, pp. 65–67 (American Public Health Association, 1979).
Hsiung et al., Diagnostic Virology, Illustrated by Light and Electron Microscopy, Third Edition, pp. 17–24 (Yale University Press, 1982).
Bach et., Immunology, pp. 845 (John Wiley & sons, 1976).
Clavel et al., The Lancet, pp. 879–880 (1985).
Brucker et al., The Lancet, p. 223 (1987).
Gallo et al., Nature, 326, pp. 435–436 (1987).
Allain et al., The Lancet, 2(8518), pp. 1233–1236 (1986).
Montagnier et al., AIDS: The Safety of Blood and Blood Products, Petricciani et al., eds., pp. 1–10 (World Health Organization, John Wiley & Sons, 1987).
Montagnier et al., Virology, 144, pp. 283–289 (1985).
Rasheed et al., Virology, 150, pp. 1–9 (1986).
Popovic et al., Nature, 300, pp. 63–66 (1982).
Gazzard et al., The Lancet, pp. 480–483 (1984).
Chermann et al., Antibiot. Chemother., vol. 32, pp. 48–53 (Karger, Basel 1984).
Maurice, "Aids investigators identify second retrovirus," JAMA, vol. 250, No. 8, pp. 1010–1015, (Aug. 26, 1983).
Ragni et al., The Lancet, pp. 213–214 (Jan. 29, 1983).
Friedman–Kien, et al., Annals of Internal Medicine, vol. 96, No. 6 (Part 1), pp. 693–700 (Jun. 1982).
Gotlieb et al., The New England Journal of Medicine, vol. 305, No. 24, pp. 1425–1431 (Dec. 10, 1981).
Stahl et al., The American Journal of Medicine, vol. 73, pp. 171–178 (Aug. 1982).
Follansbee et al., Annals of Internal Medicine, 96 (Part 1), pp. 705–713 (1982).
Francioli et al., Antibiot. Chemother., vol. 32, pp. 147–152 (Karger, Basel 1984).
Pitchenik et al., Annals of Internal Medicine, vol. 98, No. 3, pp. 277–284 (Mar. 1983).
Krasnoff et al., Hospital Pharmacy, vol. 17, No. 10, pp. 598–604 (J.B. Lippincott Co., 1982).
Wormser et al., Annals of Internal medicine, 98, pp. 297–303 (1983).
Civantos et al., The Journal of Investigative Dermatology, 79:79–80 (1982).
Mansur et al., Annals of Internal Medicine, 97:533–539 (1982).
Landay et al., The Journal of Clinical Investigation, vol. 71, pp. 1500–1504 (May 1983).
Oleske et al., JAMA, vol. 249, No. 17, pp. 2345–2349 (May 6, 1983).
Quagliarello, The Yale Journal of Biology and Medicine 55:443–452 (1982).
Man–Chiu Poon et al., Annals of Internal Medicine, 98:287–290 (1983).
Fahey et al., The New England Journal of Medicine, vol. 308, No. 14, pp. 842–843 (Apr. 7, 1983).
Gerstoft et al., British Medical Journal, vol. 285, pp. 17–19 (Jul. 3, 1982).

METHODS AND KITS FOR DETECTING ANTIBODIES AGAINST AN HIV VARIANT

This is a continuation of application Ser. No. 08/424,631, filed Apr. 19, 1995, which is a divisional of application Ser. No. 08/019,297, filed Feb. 18, 1993, which is a division of application Ser. No. 07/876,297, filed Apr. 30, 1992, now abandoned, which is a continuation of application Ser. No. 07/117,937, filed Nov. 5, 1987, now U.S. Pat. No. 5,135,864, which is a continuation application of Ser. No. 06/785,638, filed Oct. 8, 1995, now U.S. Pat. No. 4,708,818, which is a continuation application of Ser. No. 06/558,109, filed Dec. 5, 1983, now abandoned, all of which are incorporated herein by reference.

The invention relates to antigens, means and methods for the diagnosis of lymphadenopathy and acquired immune deficiency syndrome.

BACKGROUND OF THE INVENTION

The acquired immune deficiency syndrome (AIDS) has recently been recognized in several countries. The disease has been reported mainly in homosexual males with multiple partners, and epidemiological studies suggest horizontal transmission by sexual routes as well as by intravenous drug administration, and blood transfusion. The pronounced depression of cellular immunity that occurs in patients with AIDS and the quantitative modifications of subpopulations of their T lymphocytes suggest that T cells or a subset of T cells might be a preferential target for the putative infectious agent. Alternatively, these modifications may result from subsequent infections. The depressed cellular immunity may result in serious opportuninistic infections in AIDS patients, many of whom develop Kaposi's sarcoma. However, a picture of persistent multiple lymphadenopathies has also been described in homosexual males and infants who may or may not develop AIDS. The histological aspect of such lymph nodes is that of reactive hyperplasia. Such cases may correspond to an early or a milder form of the disease.

SUMMARY OF THE INVENTION

It has been found that one of the major etiological agents of AIDS and of lymphadenopathy syndrom (LAS), which is often considered as a prodromic sign of AIDS. should consist of a T-lymphotropic retrovirus which has been isolated from a lymph node of a homosexual patient with multiple lymphadenopathies. The virus appears to be distinct from the human T-cell leukemia virus (HTLV) family (R. C. Gallo and M. S. Reitz, "J. Natl. Cancer Inst.", 69 (No. 6), 1209 (1982)). The last mentioned virus has been known as belonging to the so-called HTLV-1 subgroup.

The patient was a 33-year-old homosexual male who sought medical consultation in December 1982 for cervical lymphadenopathy and asthenia (patient 1). Examination showed auxillary and inguinal lymphadenopathies. Neither fever nor recent loss of weight were noted. The patient had a history of several episodes of gonorrhea and had been treated for syphilis in September 1982. During interviews he indicated that the had had more than 50 sexual partners per year and had travelled to many countries, including North Africa, Greece, and India. His last trip to New York was in 1979.

Laboratory tests indicated positive serology (immunoglobulin G) for cytomegalovirus (CMV) and Epstein-Barr virus. Herpes simplex virus was detected in cells from his throat that were cultured on human and monkey cells. A biopsy of a cervical lymph node was performed. One sample served for histological examination, which revealed follicular hyperplasia without change of the general structure of the lymph node. Immunohistological studies revealed, in paracortical area, numerous T lymphocytes (OKT3$^+$). Typing of the whole cellular suspension indicated that 62 percent of the cells were T lymphocytes (OKT3$^+$), 44 percent were T-helper cells (OKT4$^+$)$^-$, and 16 percent were suppressor cells (OKTB$^+$).

Cells of the same biopsed lymph node were put in culture medium with phytohemagglutinin (PHA), T-cell growth factor (TCGF), and antiserum to human α interferon ("The cells were grown in RPMI-1640 medium supplemented with antibiotics, $10^{-5}$M β-mercaptoethanol, 10 percent fetal calf serum, 0.1 percent sheep antibody to human α interferon (neutralizing titer, 7 IU at $10^{-5}$ dilution and 10 percent TCGF, free of PHA"). The reason for using the antiserum to α-interferon was to neutralize endogenous interferon which is secreted by cells chronically infected by viruses, including retroviruses. In the mouse system, it had previously been shown that anti-serum to interferon could increase retrovirus production by a factor of 10 to 50 (F. Barré-Sinoussi et al., "Ann. Microbiol. (Institut Pasteur)" 130B, 349 (1979). After 3 days, the culture was continued in the same medium without PHA. Samples were regularly taken for reverse transcriptase assay and for examination in the electron microscope.

After 15 days of culture, a reverse transcriptase activity was detected in the culture supernatant by using the lionic conditions described for HTLV-I (B. J. Poiesz et al. "Proc. Natl. Acad. Sci. U.S.A." 77, 7415 (1980)). Virus production continued for 15 days and decreased thereafter, in parallel with the decline of lymphocyte proliferation. Peripheral blood lymphocytes cultured on the same way were consistently negative for reverse transcriptase activity, even after 6 weeks. Cytomegalovirus could be detected, upon prolonged co-cultivation with MRC5 cells, in the original biopsy tissue, but not in the cultured T lymphocytes at any time of the culture.

BRIEF DESCRIPTION OF THE DRAWING

This invention will be more fully described with reference to the FIGURE, which shows curves representative of reverse transcriptase activity and tritium-containing uridine activity as a function of successive fractions of LAV virus in a sucrose gradient.

DETAILED DESCRIPTION

Figure 1:
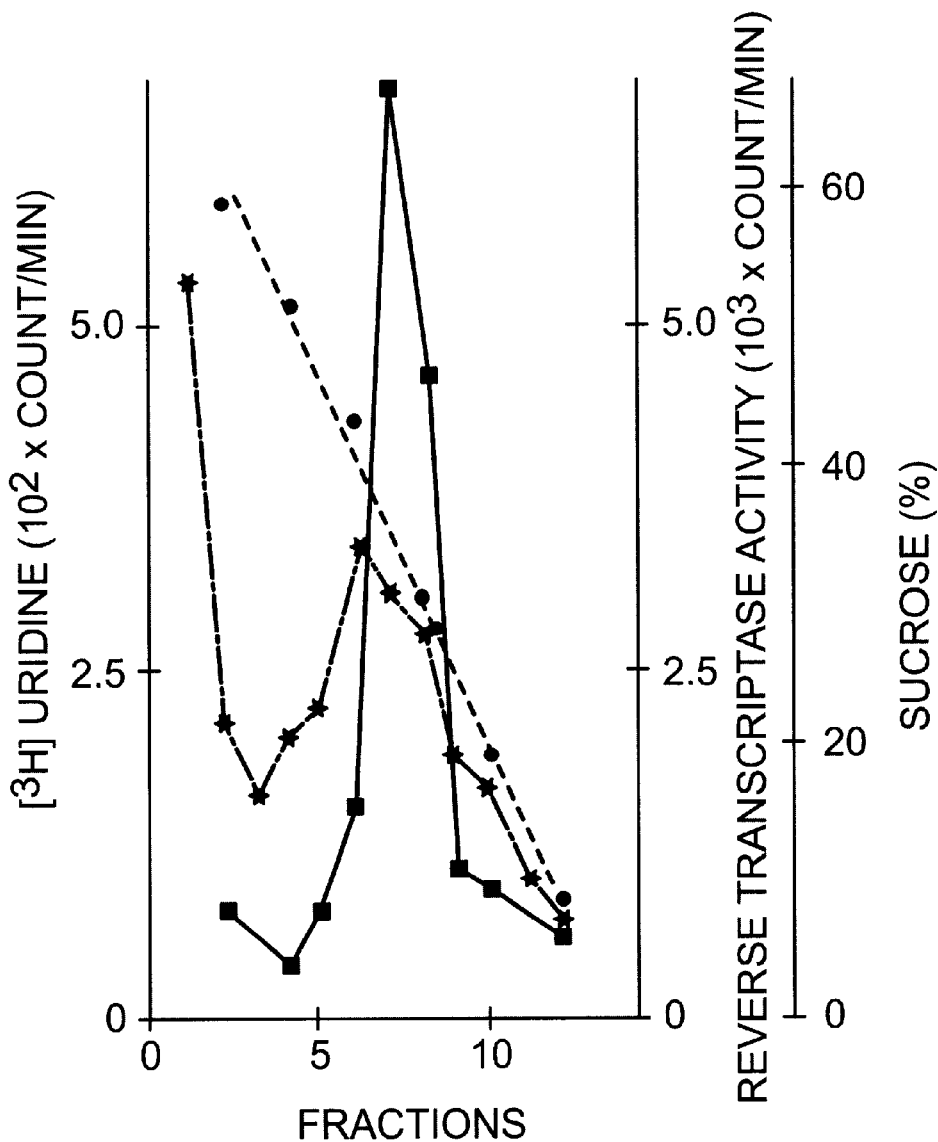

The invention relates to the newly isolated virus as a source of the above said antigen which will be defined later.

The newly isolated virus, which will hereafter be termed as LAV$_1$, will however be described first.

The virus is transmissible to cultures of T lymphocytes obtained from healthy donors. Particularly virus transmission was attempted with the use of a culture of T lymphocytes established from an adult healthy donor of the Blood Transfusion Center at the Pasteur Institute. On day 3, half of the culture was co-cultivate with lymphocytes from the biopsy after centrifugation of the mixed cell suspensions. Reverse transcriptase activity could be detected in the supernatant on day 15 of the coculture but was not detectable on days 5 and 10. The reverse transcriptase had the same characteristics as that released by the patient's cells and the amount released remained stable for 15 to 20 days. Cells of the uninfected culture of the donor lymphocytes did not release reverse transcriptase activity during this period or up to 6 weeks when the culture was discontinued.

The cell-free supernatant of the infected coculture was used to infect 3-day-old cultures of T lymphocytes from two umbilical cords, LC1 and LC5, in the presence of Polybrene (2 µg/ml). After a lag period of 7 days, a relatively high titer of reverse transcriptase activity was detected in the supernatant of both cord lymphocyte cultures. Identical cultured, which had not been infected, remained negative. These two successive infections clearly show that the virus could be propagated on normal lymphocytes from either new-borns or adults.

In the above co-cultures one used either the cells of patient 1 as such (they declined and no longer grew) or cells which had been pre-X-rayed or mitomycin C-treated.

The $LAV_1$ virus, or $LAV_1$ virus suspensions, which can be obtained from infected cultures of lymphocytes have characteristics which distinguish them completely from other HTLV. These characteristics will be referred to hereafter and, when appropriate, in relation to the drawing. It shows curves representative of variation of reverse transcriptase activity and [$^3$H]uridine activity respectively versus successive fractions of the $LAV_1$ virus in the sucrose gradient, after ultracentrifugation therein of the virus contents of a cell-free supernatant obtained from a culture of infected lymphocytes.

The analysis of $LAV_1$ virus by resorting to reverse transcriptase activity can be carried out according to the procedure which was used in relation to virus from patient 1, on FIG. 1. The results of the analysis are illustrated on FIG. 1. Cord blood T lymphocytes infected with virus from patient 1 were labelled for 18 hours with [$^3$H]uridine (28 Ci/mmol, Amersham; 20 µCi/ml). Cell-free supernatant was ultracentrifuged for 1 hour at 50,000 rev/min. The pellet was resuspended in 200 µl of NTE buffer (10 mM tris, pH 7.4, 100 mM NaCl, and 1 mM EDTA) and was centrifuged over a 3-ml linear sucrose gradient (10 to 60 percent) at 55,000 rev/min for 90 minutes in an IEC type SB 498 rotor. Fractions (200 µl) were collected, and 30 µl samples of each fraction were assayed for DNA RNA dependant polymerase activity with 5 mM $Mg^{2+}$ and poly(A)-oligo-(dT)$_{12-18}$ as template primer; a 20-µl portion of each fraction was precipitated with 10 percent trichloroacetic acid and then filtered on a 0.45-µm Millipore filter. The $^3$H-labelled acid precipitable material was measured in a Packard β counter.

That the new virus isolate was a retrovirus was further indicated by its density in the above sucrose gradient, which was 1.16, and by its labelling with [$^3$H]uridine (FIG. 1). A fast sedimenting RNA appears to be associated with the $LAV_1$ virus.

Virus-infected cells from the original biopsy as well as infected lymphocytes from the first and second viral passages were used to determine the optimal requirements for reverse transcriptase activity and the template specificity of the enzyme. The results were the same in all instances. The reverse transcriptase activity displayed a strong affinity for poly(adenylate-oligodeoxythymidylate) [poly(A)-oligo(dT)$_{12-18}$], and required $Mg^{2+}$ with an optimal concentration (5 mM) and an optimal pH of 7.8. The reaction was not inhibited by actinomycin D. This character, as well as the preferential specificity for ribosendenylate-deoxythymidylate over deoxyadenylatedeoxythymidylate, distinguish the viral enzyme from DNA-dependent polymerases.

Electron microscopy of ultrathin sections of virus-producing cells shows two types of particles, presumably corresponding to the immature and mature forms of the virus: immature particles are budding at the cell surface, with a dense crescent in close contact with the plasma membrane. Occasionally, some particles remain in this state, while being freed from the cell surface.

Mature particles have a quite different morphology with a small, dense, eccentric core (mean diameter: 41 nM). Most of virions are round (mean diameter: 139 nM) or ovoid, but in some pictures, especially in the particles seen in the original culture from which the virus was isolated, a tailed morphology can also be observed. The latter form can also be observed in cytoplasmic vesicles which were released in the medium. Such particles are also formed by budding from vesicle membranes.

Morphology of mature particles is clearly distinct from HTLV, whose large core has a mean diameter of 92 nM.

Helper T-lymphocytes (Leu3 cells) form the main target of the virus. In other words the $LAV_1$ virus has particular tropism for these cells. Leu 3 cells are recognizable by the monoclonal antibodies commercialized by ORTHO under the trademark OKT4. In contrast enriched cultures of Leu 2 cells, which are mainly suppressor or cytotoxic cells and which are recognized by the monoclonal antibodies commercialized by ORTHO under the trademark OKT8 did not produce, when infected under the same conditions, any detectable RT activity even 6 weeks after virus infection.

In most cases of AIDS, the ratio of OKT4$^+$ over OKT8$^+$ cells which is normally over 1, is depressed to values as low as 0.1 or less.

The $LAV_1$ virus is also immunologically distinct from previously known HTLV-1 isolates from cultured T lymphocytes of patients with T lymphomas and T leukemias. The antibodies used were specific for the p19 and p24 core proteins of HTLV-1. A monoclonal antibody of p19 (M. Robert-Guroff et al. "J. Exp. Med." 154, 1957 (1981)) and a polyclonal goat antibody to p24 (V. S. Kalyanaraman et al. "J. Virol.", 328, 906 (1981)) were used in an indirect fluorescence assay against infected cells from the biopsy of patient 1 and lymphocytes obtained from a healthy donor and infected with the same virus. The $LAV_1$ virus-producing cells did not react with either type of antibody, whereas two lines of cord lymphocytes chronically infected with HTVL 1 (M. Popovic, P. S. Sarin, M. Robert-Guroff, V. S. Kalyanaraman, D. Mann, J. Minowada, R. C. Gallo, "Science" 219, 856 (1983)) and used as controls showed strong surface fluorescence.

In order to determine which viral antigen was recognized by antibodies present in the patient's sera, several immunoprecipitation experiments were carried out. Cord lymphocytes infected with virus from patient 1 and uninfected controls were labelled with [$^{35}$S]methionine for 20 hours. Cells were lysed with detergents, and a cytoplasmic S10 extract was made. Labelled virus released in the supernatant was banded in a sucrose gradient. Both materials were immunoprecipitated by antiserum to HTVL-1' p24, by serum from patient 1, and by serum samples from healthy donors. Immunocomplexes were analyzed by polyacrylamide gel electrophoresis under cenaturing conditions. A p25 protein present in the virus-infected cells from patient 1 and in LC1 cells infected with this virus, was specifically recognized by serum from patient 1 but not by antiserum to HTLV-1 p24 obtained under similar conditions or serum of normal donors. Conversely the p24 present in control HTLV-infected cell extracts was recognized by antibodies to HTLV but not by serum from patient 1.

The main protein (p25) detected after purification of $^{35}$S-methionine-labelled virus has a molecular weight of about 25,000 (or 25K). This is the only protein recognized by the serum of patient 1. By analogy with other retroviruses, this major protein was considered to be located in the viral core.

This can be confirmed in immuno-electron microscopy experiments, which show that the patient's serum can agglutinate the viral cores. Conversely, an antiserum raised in rabbit against an ether treated virus did not precipitate the p25 protein.

The viral origin of other proteins seen in polyacrylamide gel electrophoresis of purified virus is more difficult to assess. A p15 protein could be seen after silver staining, but was much weaker after $^{35}$S-methionine perhaps due to the paucity of this amino-acid in the protein. In the higher MW range, a contamination of the virus by cellular proteins, either inside or outside the viral envelope, is likely. A 36K and a 42K protein and a 80K protein were constantly found to be associated with the purified virus and may represent the major envelope proteins.

Ndp19 (or having a molecular weight of about 19,000 was isolated from $LAV_1$ extracts.

The invention concerns more particularly the extracts of said virus as soon as they can be recognized immunologically by sera of patients afflicted with LAS or AIDS. Needless say any type of immunological assay may be brought into play. By way of example immunofluorescence or immunoenzymatic assays or radio-immunoprecipitation tests are particularly suitable.

As a matter of fact and except under exceptional circumstances, sera of diseased patients do not recognize the intact $LAV_1$ virus, or viruses having similar phenotypical or immunological properties. The envelope proteins of the virus appeared as not detectable immunologically by the patients' sera. However as soon as the core proteins become exposed to said sera, the immunological detection becomes possible. Therefore the invention concerns all extracts of the virus, whether it be the crudest ones—particularly mere virus lyzates —or the more purified ones, particularly extracts enriched in the p25 protein or even the purified p25 protein or in protein immunologically related therewith. Any purification procedure may be resorted to. By way of example only, one may use purification procedures such as disclosed by B. C. Montelero et al, J. of Virology, June 1982, pp. 1029–1038.

The invention concerns more generally extracts of any virus having similar phenotype and immunologically related to that obtained from $LAV_1$. Sources of viruses of the LAV type consist of T-lymphocyte cultures isolatable from LAS- and AIDS—patients or from haemophiliacs.

In that respect other preferred extracts are those obtained from two retroviruses obtained by propagation on normal lymphocytes of the retroviruses isolated from:
1) lymph node lymphocytes of a caucasian homosexual with multiple partners, having extensive Kaposi sarcoma lesions and severe lymphopenia with practically no OKT4$^+$ lymphocytes in his blood;
2) blood lymphocytes of a young B haemophillac presenting neurotoxoplasmosis and OKT4$^+$/OKT8$^+$ ratio of 0.1.

These two retroviruses have been named IDAV1 and IDAV2 respectively (for Immune Deficiency Associated Virus). Results of partial characterization obtained so far indicate similarity—if not identity—of IDAV1 and IDAV2 to LAV1:
same ionic requirements and template specificities of reverse transcriptase.
same morphology in ultrathin sections.
antigenically related p25 proteins: serum of LAV1 patient immunoprecipitates p25 from IDAV1 and IDAV2; conversely, serum from IDAV2 patient immunoprecipitates LAV1 p25.

IDAV1 patient serum seemed to have a lower antibodies titer and gave a weak precipitation band for LAV1 and IDAV1 p25 proteins. The p25 protein of IDAV1 and IDAV2 was not recognized by HTLV p24 antiserum.

These similarities suggest that all these three isolates belong to the same group of viruses.

The invention further relates to a method of in vitro diagnosis of LAS or AIDS, which comprises contacting a serum or other biological medium from a patient to be diagnosed . . . with a virus extract as above defined and detecting the immunological reaction.

Preferred methods brig into play immunoenzymatic or immunofluorescent assays, particularly according to the ELISA technique. Assays may be either direct or indirect immunoenzymatic or immunofluorescent assays.

Thus the invention also relates to labelled virus extracts whatever the type of labelling: enzymatic, fluorescent, radioactive, etc..

Such assays include for instance:
depositing determined amounts of the extract according to the invention in the wells of titration microplate;
introducing in said wells increasing dilutions of the serum to be diagnosed;
incubating the microplate;
washing the microplate extensively;
introducing in the wells of the microplate labelled antibodies directed against blood immunoglobulines, and labelling being by an enzyme selected among those which are capable of hydrolysing a substrate, whereby the latter then undergoes a modification of its absorption of radiations, at least in a determined wavelength band and
detecting, preferably in a comparative manner with respect to a control, the amount of substrate hydrolysis as a measure of the protential risks or effective presence of the disease.

The invention also relates to kits for the abovesaid diagnosis which comprise:
an extract or more purified fraction of the abovesaid types of viruses, said extract or fraction being labelled, such as by a radioactive, enzymatic or immunofluorescent label;
human anti-immunoglobulins or protein A (advantageously fixed on a water-insoluble support such as agarose beads);
a lymphocyte extract obtained from a healthy person;
buffers and, if appropriate, substrates for the vizualization of the label.

Other features of the invention will further appear as the description proceeds of preferred isolation and culturing procedures of the relevant virus, of preferred extraction methods of an extract suitable as diagnostic means, of a preferred diagnosis technique and of the results that can be achieved.

1. VIRUS PROPAGATION

Cultured T-lymphocytes from either umbilical cord or blood, or also bone marrow cells from healthy, virus negative, adult donors are suitable for virus propagation.

There is however some variation from individual to individual in the capacity of lymphocytes to grow the virus. Therefore, it is preferable to select an adult healthy donor, which had no antibodies against the virus and whose lymphocytes repeatly did not release spontaneously virus, as detected by reverse transcriptase activity (RT) nor expressed viral proteins.

Lymphocytes of the donor were obtained and separated by cytophoresis and stored frozen at −180° C. in liquid nitrogen, in RPMI 1640 medium, supplemented with 50% decomplemented human serum and 10% DMSO until used.

For viral infection, lymphocytes were put in culture (RPMI 1640 medium) with phytohaemogglutinin (PHA) at the concentration of $5 \times 10^6$ cells/ml for 3 days.

Then, the medium was removed and cells resuspended in viral suspension (crude supernatant of virus-producing lymphocytes, stored at −80° C.). Optimal conditions of cell/virus concentrations were $2 \times 10^6$ cells for 5 to 10,000 cpm of RT activity, the latter determined as previously described. After 24 hours, cells were centrifuged to remove the unadsorbed virus and resuspended in culture PHA-free medium and supplemented with PHA-free TCGF (Interleukin 2): (0.5–1 U/ml, final concentrations), POLY-BREN (Sigma) 2 µg/ml and anti-interferon a sheep serum, inactivated at 56° C. for 30 minutes (0.1% of a serum which is able to neutralize 7U of a leucocyte interferon at a 1/100,000 dilution).

Virus production was tested every 3 days by RT activity determination on 1 ml samples.

The presence of anti-interferon serum is important in virus production: when lymphocytes were infected in the absence of anti-human-α-interferon serum, virus production, as assayed by RT activity, was very low or delayed. Since the sheep antiserum used was raised against partly purified a leucocyte interferon, made according to the Cantell technique, the role of components other than interferon cannot be excluded.

Virus production starts usually from day 9 to 15 after infection, and lasts for 10–15 days. In no cases, the emergence of a continuous permanent line was observed.

2. VIRUS PURIFICATION

For its use in ELISA, the virus was concentrated by 10% Polyethylenglycol (PEG 6000) precipitation and banded twice to equilibrium in a 20–60% sucrose gradient. The viral band at density 1.16 is then recovered and usable as such for ELISA assays.

For use in RIPA radio-immune precipitation assay, purification in isotonic gradients of Metrizamide (sold under the trademark HYCODENZ by Nyegaard, Oslo) were found to be preferable. Viral density in such gradients was very low (1:10–1.11).

Metabolic labelling with $^{35}$S-methionine of cells and virus (RIPA) followed by polyacrylamide gel electrophoresis were performed as above described, except the following modifications for RIPA: virus purified in HYCODENZ who lysed in 4 volumes of RIPA containing 500 U/ml of aprotinin. Incubation with 5 µl of serum to be tested was made for 1 hour at 37° C. and then 18 hours at +4° C. Further incubation of the immunocomplexes with protein A SEPHAROSE beads was for 3 hours at +4° C.

3. PREPARATION OF THE VIRUS EXTRACT FOR ELISA ASSAYS

Virus purified in sucrose gradient as above described, is lysed in RIPA buffer (0.5% SDS) and coated on wells of microtest plates (Nunc).

Preferred conditions for the ELISA assay are summed up hereafter.

After addition to duplicate wells of serial dilutions of each serum to be tested, the specifically fixed IgGs are revealed by goat anti-human IgG coupled with peroxydase. The enzymatic reaction is carried out on ortho-phenylenediamine as substrate and read with an automatic spectrophotometer at 492 nM.

On the same plate each serum is tested on a control antigen (a crude cytoplasmic lysate of uninfected T-lymphocytes from the same donor) is used in order to eliminate unspecific binding, which can be high with some sera.

Sera are considered as positive (antibodies against the virus) when the difference between O.D. against the viral antigen and O.D. against control cellular antigen was at least 0.30.

Hereafter there is disclosed a specific test for assaying the above mentioned disease or exposure to disease risks.

Method

This ELISA test is for detecting and titration of seric anti-retrovirus type LAV antibodies.

It comprises carrying out a competition test between a viral antigen (cultivated on T lymphocytes) and a control antigen constituted by a lysate of the same through non-infected lymphocytes.

The binding of the antibodies on the two antigens is revealed by the use of a human antiglobulin labelled with an enzyme which itself is revealed by the addition of a corresponding substrate.

Preparation of the Viral Antigen

The cellular cultures which are used are T lymphocytes of human origin which come from:
umbilical cord blood,
bone marrow,
blood of a healthy donor.

After infection of the cells by the virus, the supernatant of the infected cell culture is used. It is concentrated by precipitating with 10% PEG, then purified (two or three times) on a (20–60%) sucrose gradient by ultracentrifugation to equilibrium.

The viral fractions are gathered and concentrated by centrifugation at 50 000 rotations per minute for 60 minutes.

The sedimented virus is taken in a minimum volume of buffer HTE at pH 7.4 (Tris 0.01M, NaCl 0.1M, EDTA 0.001M).

The proteic concentration is determined by the Lowry method.

The virus is then lysed by a (RIPA+SDS) buffer (0.5% final) for 15 minutes at 37° C.

Preparation of the Control Antigen

The non-infected lymphocytes are cultured according to the preceeding conditions for from 5 to 10 days. They are centrifuged at low speed and lysed in the RIPA buffer in the presence of 5% of the product commercialized under the name of ZYMOFREN (Special (500 µ/ml). After a stay of 15 minutes at 4° C. with frequent stirrings with vortex, the lysate is centrifuged at 10 000 rotations per minute. The supernatant constitutes the control antigen. Its concentration in protein is measured by the Lowry method.

Reagents

1—Plates=NUNC–special controlled ELISA
2—Buffer PBS: pH 7.5
3—TWEEN 20
4—Carbonate buffer: pH=9.6 ($CO_3Ha_2$=0.2M ($CO_3HN_a$=0.2M
5—Non foetal calf serum: which is stored in frozen state (BIOPRO).
6—Bovine serum albumine (BSA) SIGMA (fraction V)
7—Human anti IgG (H+L) labelled with peroxydase PASTEUR, in tubes of 1 ml preserved at 4° C.
8—Washing buffer=PBS buffer, pH 7.5+0.05% TWEEN 20
Dilution of the conjugate is carried out at the dilution indicated in PBS buffer+TWEEN 20 (0.05%)+bovine albumine 0.5 g per 100 ml
9—Dilution buffer of sera=PBS buffer+0.05% TWEEN 20–0.5 g BSA bovine serum albumine per 100 ml 10—Substrate=OPD Citrate buffer pH=5.6 trisodic citrate ($C_6H_5Na_4O_3$, $2H_2O$), 0.05M; citric acid ($C_6H_8O_7$, $1H_2O$), 0.05M.

Hydrogen peroxyde=at 30% (110 volumes)–used at 0.03% when using citrate buffer.

Orthophenylene diamine=SIGMA 75 mg per 25 ml of buffer—which is diluted in buffer extemporaneously.

Preparation of the Plates

The plates which are used have 96U-shaped wells (NUNC=ELISA). They include 12 rows of 8 wells each, numbered from 1 to 12.

The distribution of antigens is as follows:

100 μl of the viral antigen, diluted in carbonate buffer at pH 9.6, are deposited in each of the wells of rows (marked Θ)
1-2-5-6-9-10

100 μl of the control antigen, diluted in carbonate buffer at pH 9.6, are deposited in each of the wells of rows (marked Θ)
3-4-7-8-11-12.

The dilution of the viral antigen is titrated at each viral production. Several dilutions of viral antigen are tested and compared to positive and negative known controls (at several dilutions) and to human anti-IgG labelled with peroxydase, the latter being also tested at several dilutions.

As a rule, the proteic concentration of the preparation is of 5 to 2.5 μg/ml.

The same proteic concentration is used for the control antigen.

The plates are closed with a plastic lid and are incubated overnight at 4° C.

Then they are put once in distilled water and centrifuged. The wells are then filled with 300 μl of non foetal calf serum at 20% in PBS buffer.

The incubation lasts 2 hours at 37° C. (covered plates).

The plates are washed 3 times in PBS buffer with TWEEN 20, 0.05% (PBS-tw buffer):

first washing 300 μl second and third washing 200 μl/well.

The plates are carefully dried and sealed with an adhesive plastic film. They can be stored at −80° C.

ELISA Reaction: Antibody Titer Assay

After defreezing, the plates are washed 3 times in PBS-TWEEN. They are carefully dried.

The positive and negative control sera as well as the tested sera are diluted first in the tube, with PBS-TWEEN containing 0.5% bovine albumine.

The chosen dilution is 1/40.

100 μl of each serum are deposited in duplicate on the viral antigen and in duplicate on the control antigen.

the same is carried out for the positive and negative diluted sera.

100 μl of PBS+TWEEN+bovine serum albumine are introduced in two wells Θ and in two wells Θ to form the conjugated controls.

The plates equipped with their lids are incubated for 1.5 h at 37° C.

They are washed 4 times in PBS+TWEEN 0.05%. −100 μl of human anti-IgG (labelled with peroxydase) at the chosen dilution are deposited in each well and incubated at 37° C.

The plates are again washed 5 times with the (PBS+TWEEN) buffer. They are carefully dried.

Revealing the enzymatic reaction is carried out by means of a orthophenylene-diamine substrate (0.05% in citrate buffer pH 5.6 containing 0.03% of $H_2O_2$).

100 μl of substrate are distributed in each well.

The plates are left in a dark room 20 minutes at the laboratory temperature.

Reading is carried out on a spectrophotometer (for microplates) at 492 nm.

Sera deemed as containing antibodies against the virus are those which give a ODD (optical density difference=optical density of viral antigen less optical density of control antigen) equal or higher to 0.30.

This technique enables a qualitative titration as well as a quantitative one. For this purpose, it is possible either to use several dilutions of the serum to be assayed, or to compare a dilution of the serum with a range of controls tested under the same conditions.

The table hereafter provides first results of serological investigations for LAV antibodies, carried out by using the above exemplified ELISA assay.

FIRST RESULTS OF SEROLOGICAL INVESTIGATIONS FOR LAV ANTIBODIES IN FRANCE

|  | Total examined | ELISA-LAV positive | % positive | ELISA-HTLV1** (Biotech) positive | % positive |
|---|---|---|---|---|---|
| Lymphadeno-pathy patients* | 35 | 22 | (63) | 5*** | (14) |
| Healthy homosexuals | 40 | 7 | (17) | 1 | (3) |
| Control population | 54 | 1 | (1,9) | 0 | (<2,6) |

*28 homosexuals
3 Haitians (1 woman)
4 toxicomans (2 women)
**The number of positive sera is probably overestimated in this test, since no control of unspecific binding could be done.
***Out of the 5 LAS HTLV1 positive, 3 were born in Haiti, 1 had stayed for a long time in Haiti and 1 had made several travels to USA. All of them had also antibodies against LAV.

The table shows clearly high prevalence of LAV antibodies in the homosexual patients with LAS, the very low incidence in the normal population and also a moderate spread of virus infection in still healthy homosexuals. In the latter group, all the positive individuals had a high number of partners (>50 per year). The incidence of HTLV antibodies was very low in all three groups (determined by using a commercial ELISA test (Biotech)). The groups of AIDS patients gave less interpretable results: approximatively 20% had LAV antibodies, but some of the sera were taken at a very late stage of the disease, with a possible negativation of the humoral response.

It should further be mentioned that lymphocytes of all LAS patients do not produce detectable amounts of LAV-type virus. Particularly cells of lymph nodes from 6 more LAS patients were put in culture and tested for virus production, as described for patient 1. No virus release could be detected by RT activity. However, a p25 protein recognized by the serum of the first patient could be detected in cytoplasmic extracts of the T-cells labelled with $^{35}$S-methionine in 3 other cases. This suggests partial expression of a similar virus in such cases. Moreover, all (6/6) of these patients had antibodies against LAV p25 proteins, indicating that they all had been infected with a similar or identical virus.

Interestingly, in lymphocytes of one of the patients (patient 2), there was a weak but definite immunoprecipitation of a band of similar size (p24–p25) with goat antiserum raised against HTLV1. Similarly, the patient's serum had antibodies against both HTLV and LAV, suggesting a double infection by both viruses. Such cases seem rather infrequent.

The invention finally also relates to the biological reagents that can be formed by the LAV extracts containing the p25 protein or by the purified p25 protein, particularly for the production of antibodies directed against p25 in animals or of monoclonal antibodies. These antibodies are liable of forming useful tools in the further study of antigenic determinants of LAV viruses or LAV-related viruses.

It is acknowledged that the OKT designations which have been used with respect to the designation of some sub-sets of lymphocytes or related monoclonal antibodies by way of ease of language, should in no way be opposed to the validity of any corresponding trademark, whether registered or not by its owner.

It should further be mentioned that the viral extracts, particularly viral lysates or enriched fractions can also be defined by reference to their immunological relationship or similitude with the extracts or enriched fractions containing a p25 protein as obtainable from the strain LAV1, IDAV1 or IDAV2. Thus any protein fraction which is capable of giving similar patterns of immunological reaction as do the protein extracts of LAV1, IDAV1 or IDAV2 with the same sera, must be considered as equivalent thereof and, accordingly, be deemed as encompassed by the scope of the claims which follow. A similar conclusion extends of course to the diagnostic means (process and kits) which may make use of such equivalent protein extracts.

The LAV1 virus has been deposited at the "Collection Nationale des Cultures de Micro-organismes" (C.N.C.M.) under n° I-232 on Jul. 14, 1983 and IDAV1 and IDAV 2 viruses have been deposited at the C.N.C.M., Institut Pasteur, 28 rue de Docteur Roux, 75724 Paris Cedex 15, France, on Sep. 15, 1983 under n° I-240 and I-241, respectively. The invention encompasses as well the extracts of mutants of variants of the above deposited strains as long as they possess substantially the same immunological properties.

We claim:

1. A method for the in vitro identification of human immunodeficiency virus type 1 (HIV-1) comprising:
   subjecting cultures of infected and uninfected human lymphocytes to a protein labeling reaction;
   lysing said labeled cultures of lymphocytes;
   contacting said lysed lymphocytes with patient serum comprising an antibody that binds to p25 of HIV-1 viruses to form immunocomplexes;
   separating said immunocomplexes; and
   detecting labeled proteins in said separated immunocomplexes, wherein the detection of labeled HIV-1 proteins in said infected culture is indicative of the presence of a cell infected by HIV-1 in said culture.

2. The method of claim 1, wherein said immunocomplexes are separated by precipitation with protein A.

3. The method of claim 1, wherein said labeled proteins are resolved on a plyacrylamide gel under denaturing conditions.

4. The method of claim 1, wherein said proteins are radiolabeled.

5. The method of claim 4, wherein said proteins are radiolabeled with $^{35}$S-methionine.

6. A method for the in vitro identification of a human immunodeficiency virus type 1 (HIV-1) comprising:
   contacting lysed human lymphocytes infected with HIV-1 and uninfected human lymphocytes with patient serum comprising an antibody that binds to p25 of HIV-1 viruses to form immunocomplexes;
   contacting said immunocomplexes with a fluorescently-labeled antibody that binds to said immunocomplexes; and
   determining the presence of immunocomplexes by detecting fluorescence in the infected and uninfected samples, wherein the presence of immunocomplexes is indicative of the presence of human lymphocytes infected with HIV-1.

7. A method for the in vitro identification of antibodies that bind to human immunodeficiency virus type 1 (HIV-1) in patient serum comprising:
   contacting lysed human lymphocytes infected with HIV-1 and uninfected human lymphocytes with patient serum comprising an antibody that binds to p25 of HIV-1 viruses to form immunocomplexes;
   contacting said immunocomplexes with a fluorescently-labeled antibody that binds to said immunocomplexes; and
   determining the presence of immunocomplexes by detecting fluorescence in the infected and uninfected samples, wherein the presence of immunocomplexes is indicative of the presence of antibodies that bind to human immunodeficiency virus type 1 (HIV-1) in said patient serum.

8. A method for the in vitro identification of a human immunodeficiency virus type 1 (HIV-1) comprising:
   contacting lysed human lymphocytes infected with HIV-1 and uninfected human lymphocytes with patient serum comprising an antibody that binds to p25 of HIV-1 viruses to form immunocomplexes,
   wherein said antibody is fluorescently labeled; and
   determining the presence of immunocomplexes by detecting fluorescence in the infected and uninfected samples, wherein the presence of immunocomplexes is indicative of the presence of human lymphocytes infected with HIV-1.

9. A method for the in vitro identification of a human immunodeficiency virus type 1 (HIV-1) comprising:
   contacting lysed human lymphocytes infected with HIV-1 and uninfected human lymphocytes with patient serum comprising an antibody that binds to p25 of HIV-1 viruses to form immunocomplexes;
   contacting said immunocomplexes with an enzymatically-labeled antibody that binds to said immunocomplexes; and
   determining the presence of immnocomplexes by an enzymatic reaction in the infected and uninfected samples, wherein the presence of immunocomplexes is indicative of the presence of human lymphocytes infected with HIV-1.

10. A method for the in vitro identification of antibodies that bind to human immunodeficiency virus type 1 (HIV-1) in patient serum comprising:
    contacting lysed human lymphocytes infected with HIV-1 and uninfected human lymphocytes with patient serum comprising an antibody that binds to p25 of HIV-1 viruses to form immunocomplexes;
    contacting said immunocomplexes with an enzymatically-labeled antibody that binds to said immunocomplexes; and
    determining the presence of immunocomplexes by an enzymatic reaction in the infected and uninfected samples, wherein the presence of immunocomplexes is indicative of the presence of antibodies that bind to human immunodeficiency virus type 1 (HIV-1) in said patient serum.

11. A method for the in vitro identification of a human immunodeficiency virus type 1 (HIV-1) comprising:

contacting lysed human lymphocytes infected with HIV-1 and uninfected human lymphocytes with patient serum comprising an antibody that binds to p25 of HIV-1 viruses to form immunocomplexes.

wherein said antibody is enzymatically labeled; and determining the presence of immunocomplexes by an enzymatic reaction in the infected and uninfected samples, wherein the presence of immunocomplexes is indicative of the presence of human lymphocytes infected with HIV-1.

12. A method for the in vitro identification of a human immunodeficiency virus type 1 (HIV-1) comprising:

contacting lysed human lymphocytes infected with HIV-1 and uninfected human lymphocytes with patient serum comprising an antibody that binds to p25 of HIV-1 viruses to form immunocomplexes;

contacting said immunocomplexes with a labeled antibody that binds to said immunocomplexes; and determining the presence of labeled immunocomplexes in the infected and uninfected samples, wherein the presence of immunocomplexes is indicative of the presence of human lymphocytes infected with HIV-1.

13. A method for the in vitro identification of antibodies that bind to human immunodeficiency virus type 1 (HIV-1) in patient serum comprising:

contacting lysed human lymphocytes infected with HIV-1 and uninfected human lymphocytes with patient serum comprising an antibody that binds to p25 to HIV-1 viruses to form immunocomplexes;

contacting said immunocomplexes with a labelled antibody that binds to said immunocomplexes; and determining the presence of labeled immunocomplexes in the infected and uninfected samples, wherein the presence of immunocomplexes is indicative of the presence of antibodies that bind to human immunodeficiency virus type 1 (HIV-1) in said patient serum.

14. A method for the in vitro identification of a human immunodeficiency virus type 1 (HIV-1) comprising:

contacting lysed human lymphocytes infected with HIV-1 and uninfected human lymphocytes with patient serum comprising an antibody that binds to p25 of HIV-1 viruses to form immunocomplexes, wherein said antibody is labeled; and determining the presence of labeled immunocomplexes in the infected and uninfected samples, wherein the presence of immunocomplexes is indicative of the presence of human lymphocytes infected with HIV-1.

* * * * *

UNITED STATES PATENT AND TRADEMARK OFFICE
CERTIFICATE OF CORRECTION

PATENT NO. : 6,395,495 B1
DATED : May 28, 2002
INVENTOR(S) : Luc Montagnier, Jean-Claude Chermann, Francois Barresinoussi, Christine Rouzioux, Willy Rozenbaum, Charles Dauguet, Jacqueline Gruest, Marie-Therese Nugeyre, Francoise Rey, Robert C. Gallo, Mikulas Popovic, Mangalasseril G. Sarngadhar, Claudine Axler-Bin and Solange Chamaret It is certified that error appears in the above-identified patent and that said Letters Patent is hereby corrected as shown below:

Title page,
Item [75], Inventors, after the initial "C", insert a period and after the initial "G", insert a period.

Column 11,
Line 58, "plyacrylamide" should read -- polyacrylamide --.

Column 12,
Line 50, "immnocomplexes" should read -- immunocomplexes --.

Column 13,
Line 9, "immunocomplexes." should read -- immunocomplexes, --.

Column 14,
Line 8, "labelled" should read -- labeled --.

Signed and Sealed this

Ninth Day of July, 2002

Attest:

Attesting Officer

JAMES E. ROGAN
Director of the United States Patent and Trademark Office